United States Patent
Petrov et al.

(10) Patent No.: US 12,421,182 B2
(45) Date of Patent: Sep. 23, 2025

(54) SYNTHESIS OF (E)-1,1,1,4,5,5,5-HEPTAFLUORO-4-(TRIFLUOROMETHYL)PENT-2-ENE

(71) Applicant: THE CHEMOURS COMPANY FC, LLC, Wilmington, DE (US)

(72) Inventors: Viacheslav A. Petrov, Hockessin, DE (US); Andrew Jackson, Newark, DE (US); Sheng Peng, Hockessin, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 523 days.

(21) Appl. No.: 17/794,038

(22) PCT Filed: Jan. 22, 2021

(86) PCT No.: PCT/US2021/014486
§ 371 (c)(1),
(2) Date: Jul. 20, 2022

(87) PCT Pub. No.: WO2021/150801
PCT Pub. Date: Jul. 29, 2021

(65) Prior Publication Data
US 2023/0052956 A1  Feb. 16, 2023

Related U.S. Application Data

(60) Provisional application No. 62/964,674, filed on Jan. 23, 2020.

(51) Int. Cl.
*C07C 17/278* (2006.01)
*B01J 27/12* (2006.01)
*C07C 17/04* (2006.01)
*C07C 17/25* (2006.01)

(52) U.S. Cl.
CPC ............. *C07C 17/278* (2013.01); *B01J 27/12* (2013.01); *C07C 17/04* (2013.01); *C07C 17/25* (2013.01)

(58) Field of Classification Search
CPC .................................................. C07C 17/278
See application file for complete search history.

(56) References Cited

U.S. PATENT DOCUMENTS

| | | |
|---|---|---|
| 3,258,500 A | 6/1966 | Swamer |
| 4,828,818 A | 5/1989 | Carlson |
| 5,036,036 A | 7/1991 | Lerou |
| 6,156,943 A | 12/2000 | Petrov |
| 8,148,584 B2 | 4/2012 | Hedrick |
| 8,461,401 B2 | 6/2013 | Tung |
| 9,174,896 B2 | 11/2015 | Nappa |
| 2007/0152200 A1* | 7/2007 | Hedrick ............ A62D 1/00 252/601 |

FOREIGN PATENT DOCUMENTS

| | | |
|---|---|---|
| CN | 102884030 B | 11/2015 |
| CN | 103209943 | 11/2015 |
| EP | 486333 A1 | 10/1991 |
| WO | 200857513 A1 | 5/2008 |
| WO | 2016069242 A1 | 5/2016 |
| WO | 2018022500 A1 | 2/2018 |
| WO | 2018224908 A1 | 12/2018 |

* cited by examiner

*Primary Examiner* — Medhanit W Bahta

(57) ABSTRACT

The present application relates to processes of preparing (E)-1,1,1,4,5,5,5-heptafluoro-4-(trifluoromethyl)pent-2-ene.

5 Claims, No Drawings

SYNTHESIS OF (E)-1,1,1,4,5,5,5-HEPTAFLUORO-4-(TRIFLUOROMETHYL)PENT-2-ENE

CROSS REFERENCE TO RELATED APPLICATIONS

This application is a national filing under 35 U.S.C. 371 of International Application No. PCT/US2021/014486 filed Jan. 22, 2021, and claims priority of U.S. Provisional Application No. 62/964,674 filed Jan. 23, 2020, the disclosures of which are incorporated herein by reference in its entirety.

TECHNICAL FIELD

The present application relates to processes of preparing (E)-1,1,1,4,5,5,5-heptafluoro-4-(trifluoromethyl)pent-2-ene.

BACKGROUND

A growing public awareness of the environmental impacts from the extraction, transportation and use of fossil fuels are motivating a new environmental sustainability driver in the form of regulations and reduction in output of $CO_2$ equivalence in the atmosphere. New working fluids with low global warming potentials (GWP) and ozone depletion potential (ODP) for both existing and new applications in thermal management segments will need to adhere to these new regulations.

SUMMARY

The present application provides, inter alia, processes of preparing (E)-1,1,1,4,5,5,5-heptafluoro-4-(trifluoromethyl)pent-2-ene, comprising reacting hexafluoroprop-1-ene with 1,3,3,3-tetrafluoroprop-1-ene in the presence of an acid catalyst.

The present application further provides processes of preparing (E)-1,1,1,4,5,5,5-heptafluoro-4-(trifluoromethyl)pent-2-ene, comprising fluorinating 2,4-dichloro-1,1,1,5,5,5-hexafluoro-2-(trifluoromethyl)pentane in the presence of a catalyst.

The present application further provides compositions comprising:
 (i) (E)-1,1,1,4,5,5,5-heptafluoro-4-(trifluoromethyl)pent-2-ene; and
 (ii) one or more compounds selected from:
 (Z)-1,1,1,4,5,5,5-heptafluoro-4-(trifluoromethyl)pent-2-ene; hexafluoroprop-1-ene; and
 1,3,3,3-tetrafluoroprop-1-ene.

The present application further provides compositions comprising:
 (i) (E)-1,1,1,4,5,5,5-heptafluoro-4-(trifluoromethyl)pent-2-ene; and
 (ii) one or more compounds selected from:
 1,1,1,4,5,5,5-heptafluoro-2-(trifluoromethyl)pent-2-ene;
 (E)-4-chloro-1,1,1,5,5,5-hexafluoro-4-(trifluoromethyl)pent-2-ene; and
 1,1,1,5,5,5-hexafluoro-2-(trifluoromethyl)penta-2,3-diene.

The present application further provides compositions comprising:
 (i) 2,4-dichloro-1,1,1,5,5,5-hexafluoro-2-(trifluoromethyl)pentane; and
 (ii) one or more compounds selected from 2,2-dichloro-1,1,1,3,3,3-hexafluoropropane and 3,3,3-trifluoroprop-1-ene.

In some embodiments, the compositions provided herein are prepared according to one or more of the processes described herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Hydrofluoroolefins (HFOs) can be useful in a variety of applications including, but not limited to, foam blowing applications, heat transfer applications, refrigeration applications, cleaning applications, and solvent applications. Among recently developed HFOs, (E)-1,1,1,4,5,5,5-heptafluoro-4-(trifluoromethyl)pent-2-ene (i.e., F13iE or HFO-153-10mzzt) may be useful in heat transfer fluid applications (e.g., for use in batteries of electric vehicles). Accordingly, the present application provides new processes for preparing (E)-1,1,1,4,5,5,5-heptafluoro-4-(trifluoromethyl)pent-2-ene.

Definitions and Abbreviations

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consisting essentially of" is used to define a composition, method that includes materials, steps, features, components, or elements, in addition to those literally disclosed provided that these additional included materials, steps, features, components, or elements do not materially affect the basic and novel characteristic(s) of the claimed invention, especially the mode of action to achieve the desired result of any of the processes of the present invention. The term "consists essentially of" or "consisting essentially of" occupies a middle ground between "comprising" and "consisting of".

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

As used herein, the term "about" is meant to account for variations due to experimental error (e.g., plus or minus approximately 10% of the indicated value). All measurements reported herein are understood to be modified by the term "about", whether or not the term is explicitly used, unless explicitly stated otherwise.

The term "alkyl", as used herein, either alone or in combination includes cyclic or acyclic and straight-chain or branched alkyl groups, such as, methyl, ethyl, n-propyl, i-propyl, or the different isomers thereof. For example, the alkyl group may contain 1-10 carbon atoms. The alkyl group may be a lower alkyl which contains from 1 to 6 carbon atoms.

As used herein, the term "catalyst", refers to a substance that speeds up the chemical reaction, but is not consumed by the reaction, thus it can be recovered chemically unchanged at the end of the reaction.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

The following abbreviations may be used herein:
F13iE or HFO-153-10mzzt: (E)-1,1,1,4,5,5,5-heptafluoro-4-(trifluoromethyl)pent-2-ene
HCFO: hydrochlorofluoroolefin
HCFO-153-10mzzx: (E)-4-chloro-1,1,1,5,5,5-hexafluoro-4-(trifluoromethyl)pent-2-ene
HFC: hydrofluorocarbon
HCFC-216aa: 2,2-dichloro-1,1,1,3,3,3-hexafluoropropane
HFC-549mdfx: 2,4-dichloro-1,1,1,5,5,5-hexafluoro-2-(trifluoromethyl)pentane
HFO: hydrofluoroolefin
HFO-1234ze: 1,3,3,3-tetrafluoroprop-1-ene
HFO-1529mztt: 1,1,1,5,5,5-hexafluoro-2-(trifluoromethyl)penta-2,3-diene
HFO-153-10mezt: 1,1,1,4,5,5,5-heptafluoro-2-(trifluoromethyl)pent-2-ene
HFP: hexafluoropropene
TFP: 3,3,3-trifluoroprop-1-ene Processes of the Invention The present application provides processes of preparing (E)-1,1,1,4,5,5,5-heptafluoro-4-(trifluoromethyl)pent-2-ene, comprising reacting hexafluoroprop-1-ene with 1,3,3,3-tetrafluoroprop-1-ene in the presence of an acid catalyst.

In some embodiments, the acid catalyst is a Lewis acid catalyst. As used herein, the term "Lewis acid catalyst" compound (e.g., a metal based compound) that acts as an electron pair acceptor to increase the reactivity of a substrate. Exemplary Lewis acid catalysts include, but are not limited to, transition metal Lewis acid catalysts (e.g., titanium, zinc, iron, copper, and zinc based Lewis acid catalysts) and main group Lewis acid catalysts (e.g., aluminum, boron, silicon, tin, and antimony Lewis acid catalysts). In some embodiments, the acid catalyst is a strong Lewis acid catalyst. Additional examples of Lewis acid catalysts can be found, for example, in International Publication Nos.: WO 2008/057513 and WO 2018/022500, the disclosure of each of which is incorporated herein by reference in its entirety.

In some embodiments, the acid catalyst is selected from $SbF_5$, aluminum chlorofluoride (ACF), and aluminum chloride. In some embodiments, the acid catalyst is $SbF_5$.

In some embodiments, the reacting of hexafluoroprop-1-ene with 1,3,3,3-tetrafluoroprop-1-ene is performed at a temperature of from about −30° C. to about 100° C., for example, about −30° C. to about 75° C., about −30° C. to about 50° C., about −30° C. to about 25° C., about −30° C. to about 10° C., about −30° C. to about 0° C., about 0° C. to about 100° C., about 0° C. to about 75° C., about 0° C. to about 50° C., about 0° C. to about 25° C., about 0° C. to about 10° C., about 10° C. to about 100° C., about 10° C. to about 75° C., about 10° C. to about 50° C., about 10° C. to about 25° C., about 25° C. to about 100° C., about 25° C. to about 75° C., about 25° C. to about 50° C., about 50° C. to about 100° C., about 50° C. to about 75° C., or about 75° C. to about 100° C. In some embodiments, the reacting of hexafluoroprop-1-ene with 1,3,3,3-tetrafluoroprop-1-ene is performed at a temperature of from about 25° C. to about 75° C. In some embodiments, the reacting of hexafluoroprop-1-ene with 1,3,3,3-tetrafluoroprop-1-ene is performed at a temperature of from about 40° C. to about 60° C.

In some embodiments, the reacting of hexafluoroprop-1-ene with 1,3,3,3-tetrafluoroprop-1-ene is performed at a pressure of from about 1 atm to about 25 atm, for example, about 1 atm to about 20 atm, about 1 atm to about 15 atm, about 1 atm to about 10 atm, about 1 atm to about 5 atm, about 5 atm to about 25 atm, about 5 atm to about 20 atm, about 5 atm to about 15 atm, about 5 atm to about 10 atm, about 10 atm to about 25 atm, about 10 atm to about 20 atm, about 10 atm to about 15 atm, about 15 atm to about 25 atm, about 15 atm to about 20 atm, or about 20 atm to about 25 atm.

In some embodiments, the reacting of hexafluoroprop-1-ene with 1,3,3,3-tetrafluoroprop-1-ene is performed as a liquid phase reaction. In some embodiments, the reacting of hexafluoroprop-1-ene with 1,3,3,3-tetrafluoroprop-1-ene is performed in the absence of an additional solvent component.

In some embodiments, the process of preparing (E)-1,1,1,4,5,5,5-heptafluoro-4-(trifluoromethyl)pent-2-ene comprises pre-mixing the hexafluoroprop-1-ene and the acid catalyst to form a first mixture. In some embodiments, pre-mixing the hexafluoroprop-1-ene and the acid catalyst to form the first mixture is performed prior to the reacting with 1,3,3,3-tetrafluoroprop-1-ene. In some embodiments, the mixing of hexafluoroprop-1-ene and the acid catalyst is performed in the liquid phase. In some embodiments, the first mixture is a liquid.

In some embodiments, the pre-mixing of hexafluoroprop-1-ene and the acid catalyst is performed at a pressure of from about 1 atm to about 25 atm, for example, about 1 atm to about 20 atm, about 1 atm to about 15 atm, about 1 atm to about 10 atm, about 1 atm to about 5 atm, about 5 atm to about 25 atm, about 5 atm to about 20 atm, about 5 atm to about 15 atm, about 5 atm to about 10 atm, about 10 atm to about 25 atm, about 10 atm to about 20 atm, about 10 atm to about 15 atm, about 15 atm to about 25 atm, about 15 atm to about 20 atm, or about 20 atm to about 25 atm.

In some embodiments, the process comprises addition of the 1,3,3,3-tetrafluoroprop-1-ene to the first mixture, thereby forming the (E)-1,1,1,4,5,5,5-heptafluoro-4-(trifluoromethyl)pent-2-ene.

In some embodiments, the present application provides a process of preparing (E)-1,1,1,4,5,5,5-heptafluoro-4-(trifluoromethyl)pent-2-ene, comprising:
(i) pre-mixing hexafluoroprop-1-ene and $SbF_5$ to form a first mixture; and
(ii) reacting 1,3,3,3-tetrafluoroprop-1-ene with the first mixture to form the (E)-1,1,1,4,5,5,5-heptafluoro-4-(trifluoromethyl)pent-2-ene.

The present application further provides processes of preparing (E)-1,1,1,4,5,5,5-heptafluoro-4-(trifluoromethyl)pent-2-ene, comprising fluorinating 2,4-dichloro-1,1,1,5,5,5-hexafluoro-2-(trifluoromethyl)pentane in the presence of a catalyst.

In some embodiments, the fluorinating comprises reacting the 2,4-dichloro-1,1,1,5,5,5-hexafluoro-2-(trifluoromethyl)pentane in the presence of a fluorinating agent.

In some embodiments, one molar equivalent of fluorinating agent, or an excess of fluorinating agent, is used based on 1 equivalent of the 2,4-dichloro-1,1,1,5,5,5-hexafluoro-2-(trifluoromethyl)pentane. In some embodiments, one molar equivalent of fluorinating agent is used based on 1 equivalent of the 2,4-dichloro-1,1,1,5,5,5-hexafluoro-2-(trifluoromethyl)pentane. In some embodiments, a molar excess of fluorinating agent is used based on 1 equivalent of the 2,4-dichloro-1,1,1,5,5,5-hexafluoro-2-(trifluoromethyl)pentane.

In some embodiments, about 1 to about 25 molar equivalents of fluorinating agent is used based on 1 equivalent of the 2,4-dichloro-1,1,1,5,5,5-hexafluoro-2-(trifluoromethyl)pentane, for example, about 1 to about 20, about 1 to about 15, about 1 to about 10, about 1 to about 5, about 1 to about 2, about 2 to about 25, about 2 to about 20, about 2 to about 15, about 2 to about 10, about 2 to about 5, about 5 to about 25, about 5 to about 20, about 5 to about 15, about 5 to about 10, about 10 to about 25, about 10 to about 20, about 10 to about 15, about 15 to about 25, about 15 to about 20, or about 20 to about 25 molar equivalents of fluorinating agent. In some embodiments, about 6 to about 25 molar equivalents of fluorinating agent is used based on 1 equivalent of the 2,4-dichloro-1,1,1,5,5,5-hexafluoro-2-(trifluoromethyl)pentane.

In some embodiments, the fluorinating agent is selected from hydrogen fluoride, antimony trifluoride, antimony tetrafluoride, antimony pentafluoride, antimony trichloride/hydrogen fluoride, antimony tetrachloride/hydrogen fluoride, or any mixture thereof. In some embodiments, the fluorinating agent is hydrogen fluoride.

In some embodiments, the fluorinating is performed as a liquid phase fluorination.

In some embodiments, the liquid phase fluorination is performed at a temperature of from about 50° C. to about 150° C., for example, about 50° C. to about 125° C., about 50° C. to about 100° C., about 50° C. to about 75° C., about 75° C. to about 150° C., about 75° C. to about 125° C., about 75° C. to about 100° C., about 100° C. to about 150° C., about 100° C. to about 125° C., or about 125° C. to about 150° C., In some embodiments, the liquid phase fluorination is performed at a pressure of from about 0 psig to about 600 psig, for example, about 0 psig to about 500 psig, about 0 psig to about 400 psig, about 0 psig to about 300 psig, about 0 psig to about 200 psig, about 0 psig to about 100 psig, about 0 psig to about 50 psig, about 50 psig to about 600 psig, about 50 psig to about 500 psig, about 50 psig to about 400 psig, about 50 psig to about 300 psig, about 50 psig to about 200 psig, about 50 psig to about 100 psig, about 100 psig to about 600 psig, about 100 psig to about 500 psig, about 100 psig to about 400 psig, about 100 psig to about 300 psig, about 100 psig to about 200 psig, about 200 psig to about 600 psig, about 200 psig to about 500 psig, about 200 psig to about 400 psig, about 200 psig to about 300 psig, about 300 psig to about 600 psig, about 300 psig to about 500 psig, about 300 psig to about 400 psig, about 400 psig to about 600 psig, about 400 psig to about 500 psig, or about 500 psig to about 600 psig.

In some embodiments, the fluorinating is performed as a gas phase fluorination.

In some embodiments, the gas phase fluorination is performed at a temperature of from about 200° C. to about 400° C., for example, about 200° C. to about 350° C., about 200° C. to about 300° C., about 200° C. to about 250° C., about 250° C. to about 400° C., about 250° C. to about 350° C., about 250° C. to about 300° C., about 300° C. to about 400° C., about 300° C. to about 350° C., or about 350° C. to about 400° C.

In some embodiments, the gas phase fluorination is performed at a pressure of from about 0 psig to about 200 psig, for example, about 0 psig to about 150 psig, about 0 psig to about 100 psig, about 0 psig to about 50 psig, about 0 psig to about 25 psig, about 25 psig to about 200 psig, about 25 psig to about 150 psig, about 25 psig to about 100 psig, about 25 psig to about 50 psig, about 50 psig to about 200 psig, about 50 psig to about 150 psig, about 50 psig to about 100 psig, about 100 psig to about 200 psig, about 100 psig to about 150 psig, or about 150 psig to about 200 psig.

In some embodiments, the catalyst is a chromium catalyst. Exemplary chrome catalysts include, but are not limited to, chromium-based catalysts, such as chromium oxyfluoride, which catalyst may either be unsupported, or supported on a support such as activated carbon, graphite, fluoride graphite, or fluoride alumina. The chromium catalyst may either be used alone, or in the presence of a co-catalyst selected from nickel, cobalt, manganese or zinc salt. In one embodiment, a chromium catalyst is high surface area chromium oxide, or chromium/nickel on fluoride alumina (Cr/Ni/AlF$_3$), the preparation of which is reported in European Patent No.: 486,333, the disclosure of which is incorporated herein by reference in its entirety.

Chromium oxyfluoride catalysts can be made by treating $Cr_2O_3$ (chromium oxide) with HF, $CCl_3F$, or hydrofluorocarbons. In some embodiments, a chromium oxyfluoride catalyst is prepared by treating dry $Cr_2O_3$ with a fluorination agent such as $CCl_3F$ or HF. This treatment can be accomplished by placing the $Cr_2O_3$ in a suitable container (which can also be the reactor to be used to perform the fluorination reaction described herein) and thereafter passing HF over the dry $Cr_2O_3$ for a suitable period of time (e.g., about 15 to 300 minutes) at a suitable temperature (e.g., about 200° C. to 450° C.).

In some embodiments, a chromium oxyfluoride catalyst can be prepared treating $Cr_2O_3$ with a hydrofluorocarbon at an elevated temperature. In some embodiments, the chromium catalyst (e.g., chromium oxyfluoride catalyst) is prepared in situ. Exemplary methods of preparing $Cr_2O_3$ can be found in U.S. Pat. Nos. 5,036,036, 4,828,818, and 3,258,500, the disclosure of each of which is incorporated herein by reference in its entirety.

In some embodiments, the catalyst is selected from chromium oxyfluoride, chromium oxyfluoride on activated carbon, chromium oxyfluoride on graphite, chromium oxyfluoride on fluoride graphite, chromium oxyfluoride on fluoride alumina, chrome oxide, high surface area chromium oxide, fluorinated alumina, and chromium/nickel on fluoride alumina. In some embodiments, the fluorination is a liquid phase fluorination and the catalyst is a chromium catalyst. Additional examples of catalysts that may be suitable for one or more of the processes described herein can be found, for example, in International Application No.: WO 2018/022500, the disclosure of which is incorporated herein by reference in its entirety.

In some embodiments, the catalyst is activated prior to the fluorinating. In some embodiments, the activating comprises heating the catalyst to a temperature of from about 350° C. to about 400° C. for a first period of time, for example, about 350° C. to about 380° C., about 350° C. to about 360° C., about 360° C. to about 400° C., about 360° C. to about 380° C., or about 380° C. to about 400° C. In some embodiments, the heating for a first period of time is performed in the presence of nitrogen gas.

In some embodiments, the activating further comprises heating the catalyst to temperature of from about 350° C. to about 400° C. in the presence of hydrogen fluoride, for a second period of time, for example, about 350° C. to about 380° C., about 350° C. to about 360° C., about 360° C. to about 400° C., about 360° C. to about 380° C., or about 380° C. to about 400° C.

In some embodiments, the heating for a second period of time is performed in the presence of nitrogen, air, or a mixture thereof. In some embodiments, the heating for a second period of time is performed in the presence of nitrogen. In some embodiments, the heating for a second period of time is performed in the presence of air. In some embodiments, the heating for a second period of time is performed in the presence of a mixture of nitrogen and air.

In some embodiments, the 2,4-dichloro-1,1,1,5,5,5-hexafluoro-2-(trifluoromethyl)pentane is prepared according to a process comprising reacting 2,2-dichloro-1,1,1,3,3,3-hexafluoropropane with 3,3,3-trifluoroprop-1-ene in the presence of an iron catalyst and a trialkyl phosphate or phosphine ligand.

In some embodiments, the iron catalyst is iron metal. In some embodiments, the metallic iron component of the iron catalyst may be from any source (including a combination of sources) of an iron component including, but not limited to, iron powder, iron wire, iron screen, or iron turnings. In some embodiments, the iron catalyst is iron chloride. In some embodiments, the iron catalyst is iron (Ill) chloride. In some embodiments, the iron catalyst is a combination of iron metal and iron chloride. In some embodiments, the iron catalyst is a combination of iron metal and iron (Ill) chloride. Add In some embodiments, the 2,4-dichloro-1,1,1,5,5,5-hexafluoro-2-(trifluoromethyl)pentane is prepared in the presence of an iron catalyst and a trialkyl phosphate. In some embodiments, the trialkyl phosphate is a tri($C_{1-6}$ alkyl) phosphate. In some embodiments, the trialkyl phosphate (e.g., the tri($C_{1-6}$ alkyl)phosphate) is tributyl phosphate.

In some embodiments, the 2,4-dichloro-1,1,1,5,5,5-hexafluoro-2-(trifluoromethyl)pentane is prepared in the presence of an iron catalyst and a phosphine ligand. In some embodiments, the phosphine ligand is selected from an alkylphosphine or arylphosphine. Exemplary phosphine ligands include, but are not limited to, triphenyl phosphine, tributyl phosphine, and the like. Exemplary phosphine ligands can be found for example, in International Application No.: WO 2018/022500, the disclosure of which is incorporated herein by reference in its entirety.

In some embodiments, wherein the reacting of 2,2-dichloro-1,1,1,3,3,3-hexafluoropropane with 3,3,3-trifluoroprop-1-ene is performed at a temperature of from about 50° C. to about 250° C., for example, about 50° C. to about 200° C., about 50° C. to about 150° C., about 50° C. to about 100° C., about 100° C. to about 250° C., about 100° C. to about 200° C., about 100° C. to about 150° C., about 150° C. to about 250° C., about 150° C. to about 200° C., about 200° C. to about 250° C.

In some embodiments, the present application provides a process of preparing (E)-1,1,1,4,5,5,5-heptafluoro-4-(trifluoromethyl)pent-2-ene, comprising:
(i) reacting 2,2-dichloro-1,1,1,3,3,3-hexafluoropropane with 3,3,3-trifluoroprop-1-ene in the presence of iron metal and tributyl phosphate to form 2,4-dichloro-1,1,1,5,5,5-hexafluoro-2-(trifluoromethyl)pentane; and
(ii) reacting the 2,4-dichloro-1,1,1,5,5,5-hexafluoro-2-(trifluoromethyl)pentane with hydrogen fluoride in the presence of a chrome catalyst to form the (E)-1,1,1,4,5,5,5-heptafluoro-4-(trifluoromethyl)pent-2-ene.

In some embodiments, the (E)-1,1,1,4,5,5,5-heptafluoro-4-(trifluoromethyl)pent-2-ene prepared according to one or more of the processes described herein is substantially isolated. By "substantially isolated" is meant that the compound is at least partially or substantially separated from the environment in which it was formed or detected. Partial separation can include, for example, a composition enriched in (E)-1,1,1,4,5,5,5-heptafluoro-4-(trifluoromethyl)pent-2-ene. Substantial separation can include compositions containing at least about 50%, at least about 60%, at least about 70%, at least about 80%, at least about 90%, at least about 95%, at least about 97%, or at least about 99% by weight of (E)-1,1,1,4,5,5,5-heptafluoro-4-(trifluoromethyl)pent-2-ene. Methods for isolating compounds are routine in the art.

In some embodiments, the processes described herein may be conducted in a reaction zone comprising any reaction vessel of appropriate size for the scale for the reaction. In some embodiments, the reaction zone comprises a reaction vessel comprised of materials which are resistant to corrosion. In some embodiments, said materials comprise alloys, such as nickel-based alloys such as Hastelloy®, nickel-chromium alloys commercially available from Special Metals Corp. (New Hartford, New York) under the trademark Inconel®, or nickel-copper alloys commercially available from Special Metals Corp. under the trademark Monel®, or vessels having fluoropolymers linings. In some embodiments, the reaction vessel may comprise other materials of construction including, but not limited to, stainless steels, in particular of the austenitic type, and copper-clad steel.

Compositions of the Invention

The present application further provides compositions comprising one or more major components (e.g., (E)-1,1,1,4,5,5,5-heptafluoro-4-(trifluoromethyl)pent-2-ene) in combination with one or more additional compounds (i.e., minor components). The presence of the additional compounds in a sample containing one or more of the major components (e.g., (E)-1,1,1,4,5,5,5-heptafluoro-4-(trifluoromethyl)pent-2-ene) may be used, for example, to identify the process by which one or more of the major components was manufactured. In some embodiments, the compositions are prepared according to one or more of the processes described herein.

Accordingly, the present application provides compositions comprising:
(i) (E)-1,1,1,4,5,5,5-heptafluoro-4-(trifluoromethyl)pent-2-ene; and
(ii) one or more compounds selected from:
(Z)-1,1,1,4,5,5,5-heptafluoro-4-(trifluoromethyl)pent-2-ene; hexafluoroprop-1-ene; and
1,3,3,3-tetrafluoroprop-1-ene.

In some embodiments, the composition comprises about 2 to about 3 mole percent (Z)-1,1,1,4,5,5,5-heptafluoro-4-(trifluoromethyl)pent-2-ene. In some embodiments, the composition further comprises $SbF_5$.

In some embodiments, the composition comprising:
(i) (E)-1,1,1,4,5,5,5-heptafluoro-4-(trifluoromethyl)pent-2-ene; and
(ii) one or more compounds selected from: (Z)-1,1,1,4,5,5,5-heptafluoro-4-(trifluoromethyl)pent-2-ene; hexafluoroprop-1-ene; and 1,3,3,3-tetrafluoroprop-1-ene;
is prepared according to a process described herein.

In some embodiments, the composition comprises:
(E)-1,1,1,4,5,5,5-heptafluoro-4-(trifluoromethyl)pent-2-ene; and
(Z)-1,1,1,4,5,5,5-heptafluoro-4-(trifluoromethyl)pent-2-ene; hexafluoroprop-1-ene; and
1,3,3,3-tetrafluoroprop-1-ene.

In some embodiments, the composition comprising (E)-1,1,1,4,5,5,5-heptafluoro-4-(trifluoromethyl)pent-2-ene, (Z)-1,1,1,4,5,5,5-heptafluoro-4-(trifluoromethyl)pent-2-ene, hexafluoroprop-1-ene, and 1,3,3,3-tetrafluoroprop-1-ene is prepared according to a process described herein.

The present application further provides compositions comprising (E)-1,1,1,4,5,5,5-heptafluoro-4-(trifluoromethyl)pent-2-ene and 2,4-dichloro-1,1,1,5,5,5-hexafluoro-2-(trifluoromethyl)pentane. In some embodiments, the composition further comprises hydrogen fluoride, chromium oxyfluoride, or a combination thereof. In some embodiments, the composition further comprises hydrogen fluoride. In some embodiments, the composition further comprises chromium oxyfluoride. In some embodiments, the composition further comprises a combination of hydrogen fluoride and chromium oxyfluoride. In some embodiments, the composition comprising (E)-1,1,1,4,5,5,5-heptafluoro-4-(trifluoromethyl)pent-2-ene and 2,4-dichloro-1,1,1,5,5,5-hexafluoro-2-(trifluoromethyl)pentane is prepared according to a process described herein.

The present application further comprises compositions comprising:
(i) 2,4-dichloro-1,1,1,5,5,5-hexafluoro-2-(trifluoromethyl)pentane; and
(ii) one or more compounds selected from 2,2-dichloro-1,1,1,3,3,3-hexafluoropropane and 3,3,3-trifluoroprop-1-ene.

In some embodiments, the composition further comprises iron metal, iron chloride, and trialkyl phosphate (e.g., a tri($C_{1-6}$ alkyl)phosphate), or any combination thereof. In some embodiments, the composition further comprises iron metal, iron chloride, and tri($C_{1-6}$ alkyl)phosphate, or any combination thereof. In some embodiments, the composition further comprises iron metal, iron (Ill) chloride, and tributyl phosphate, or any combination thereof. In some embodiments, the composition further comprises iron metal, tributyl phosphate, or any combination thereof.

In some embodiments, the composition comprising:
(i) 2,4-dichloro-1,1,1,5,5,5-hexafluoro-2-(trifluoromethyl)pentane; and
(ii) one or more compounds selected from 2,2-dichloro-1,1,1,3,3,3-hexafluoropropane and 3,3,3-trifluoroprop-1-ene; is prepared according to a process described herein.

In some embodiments, the composition comprises:
2,4-dichloro-1,1,1,5,5,5-hexafluoro-2-(trifluoromethyl)pentane;
2,2-dichloro-1,1,1,3,3,3-hexafluoropropane; and
3,3,3-trifluoroprop-1-ene.

In some embodiments, the composition comprising 2,4-dichloro-1,1,1,5,5,5-hexafluoro-2-(trifluoromethyl)pentane, 2,2-dichloro-1,1,1,3,3,3-hexafluoropropane, and 3,3,3-trifluoroprop-1-ene is prepared according to a process described herein.

The present application further provides compositions comprising:
(i) (E)-1,1,1,4,5,5,5-heptafluoro-4-(trifluoromethyl)pent-2-ene; and
(ii) one or more compounds selected from 1,1,1,4,5,5,5-heptafluoro-2-(trifluoromethyl)pent-2-ene (HFO-153-10mezt), (E)-4-chloro-1,1,1,5,5,5-hexafluoro-4-(trifluoromethyl)pent-2-ene (HCFO-153-10mzzx), and 1,1,1,5,5,5-hexafluoro-2-(trifluoromethyl)penta-2,3-diene (HFO-1529mztt).

In some embodiments, the composition further comprises 2,4-dichloro-1,1,1,5,5,5-hexafluoro-2-(trifluoromethyl)pentane. In some embodiments, the composition further comprises hydrogen fluoride. In some embodiments, the composition further comprises a chrome catalyst as described herein.

In some embodiments, the composition comprises:
(E)-1,1,1,4,5,5,5-heptafluoro-4-(trifluoromethyl)pent-2-ene;
1,1,1,4,5,5,5-heptafluoro-2-(trifluoromethyl)pent-2-ene (HFO-153-10mezt);
(E)-4-chloro-1,1,1,5,5,5-hexafluoro-4-(trifluoromethyl)pent-2-ene (HCFO-153-10mzzx); and
1,1,1,5,5,5-hexafluoro-2-(trifluoromethyl)penta-2,3-diene (HFO-1529mztt).

In some embodiments, the composition comprising (E)-1,1,1,4,5,5,5-heptafluoro-4-(trifluoromethyl)pent-2-ene, 1,1,1,4,5,5,5-heptafluoro-2-(trifluoromethyl)pent-2-ene (HFO-153-10mezt), (E)-4-chloro-1,1,1,5,5,5-hexafluoro-4-(trifluoromethyl)pent-2-ene (HCFO-153-10mzzx), and 1,1,1,5,5,5-hexafluoro-2-(trifluoromethyl)penta-2,3-diene (HFO-1529mztt) is prepared according to a process described herein.

In some embodiments, the composition comprises:
(E)-1,1,1,4,5,5,5-heptafluoro-4-(trifluoromethyl)pent-2-ene;
1,1,1,4,5,5,5-heptafluoro-2-(trifluoromethyl)pent-2-ene (HFO-153-10mezt);
(E)-4-chloro-1,1,1,5,5,5-hexafluoro-4-(trifluoromethyl)pent-2-ene (HCFO-153-10mzzx);
1,1,1,5,5,5-hexafluoro-2-(trifluoromethyl)penta-2,3-diene (HFO-1529mztt); and
2,4-dichloro-1,1,1,5,5,5-hexafluoro-2-(trifluoromethyl)pentane.

In some embodiments, the composition comprising (E)-1,1,1,4,5,5,5-heptafluoro-4-(trifluoromethyl)pent-2-ene, 1,1,1,4,5,5,5-heptafluoro-2-(trifluoromethyl)pent-2-ene (HFO-153-10mezt), (E)-4-chloro-1,1,1,5,5,5-hexafluoro-4-(trifluoromethyl)pent-2-ene (HCFO-153-10mzzx), 1,1,1,5,5,5-hexafluoro-2-(trifluoromethyl)penta-2,3-diene (HFO-1529mztt), and 2,4-dichloro-1,1,1,5,5,5-hexafluoro-2-(trifluoromethyl)pentane is prepared according to a process described herein.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1. Preparation of (E)-1,1,1,4,5,5,5-heptafluoro-4-(trifluoromethyl)pent-2-ene (F13iE)

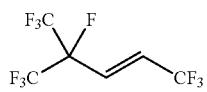

Step 1. Preparation of 2,4-dichloro-1,1,1,5,5,5-hexafluoro-2-(trifluoromethyl)pentane (HFC-549mdfx)

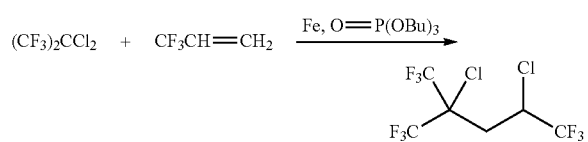

400 mL Hastelloy shaker tube was charged with 222 g of $(CF_3)_2CCl_2$ (i.e., HFC 216aa) 1 g of cut iron wire, 0.5 g of $FeCl_3$, and 3 g $O=P(OBu)_3$. The shaker tube was closed, cooled with dry ice, evacuated, and purged with nitrogen. This cycle was repeated three times. The tube was subsequently charged with 20 g of 3,3,3-trifluoroprop-1-ene (i.e., TFP). The tube was heated to 150° C. and an additional 76 g of TFP was added to the reaction vessel, and it was maintained at 150° C. for 12 h. The reactor was then unloaded at ambient temperature and 220 g of crude reaction mixture was isolated, containing ~50% of the title product. The reaction mixture was distilled at reduced to afford 75 g 2,4-dichloro-1,1,1,5,5,5-hexafluoro-2-(trifluoromethyl)pentane (yield 31%, purity 95%). $^{19}$F NMR ($CDCl_3$): −72.14 (3F, q, 10.8 Hz), −72.59(3F,q, 10.8 Hz), −75.72(3F, d, 6.7 Hz) ppm; $^1$H NMR ($CDCl_3$): 2.74 (1H, m), 2.96 (1H, m), 4.45(1H, quint., 6.8 Hz) ppm; MS (m/z): 316 (M$^+$, $C_6H_3Cl_2F_9^+$)

Step 2. Gas Phase Preparation of (E)-1,1,1,4,5,5,5-heptafluoro-4-(trifluoromethyl)pent-2-ene (F13iE)

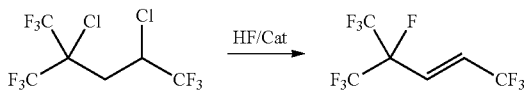

An Inconel® pipe (0.5 inch OD, 10 inch length, 0.034 in wall thickness) was filled with 4 cc chrome catalyst. The reactor was heated to a target temperature 325° C. 2,4-Dichloro-1,1,1,5,5,5-hexafluoro-2-(trifluoromethyl)pentane (96% GC purity) was fed via an ISCO pump (0.38 mL/h) and a vaporizer controlled at 140° C. HF/organics mol ratio was 15, the contact time was 10 seconds, and the reaction was performed at 0 psig. The reactor effluent was analyzed online using an Agilent® 6890 GC/5973 MS and showed 90% conversion of the starting material with 15-20% selectivity for (E)-1,1,1,4,5,5,5-heptafluoro-4-(trifluoromethyl) pent-2-ene and 55-60% selectivity to (E)-4-chloro-1,1,1,5,5,5-hexafluoro-4-(trifluoromethyl)pent-2-ene.

Observed minor products included (E)-4-chloro-1,1,1,5,5,5-hexafluoro-4-(trifluoromethyl)pent-2-ene (HCFO-153-10mzzx), 1,1,1,4,5,5,5-heptafluoro-2-(trifluoromethyl)pent-2-ene (HFO-153-10mezt), and 1,1,1,5,5,5-hexafluoro-2-(trifluoromethyl)penta-2,3-diene (HFO-1529mztt).

Example 2. Alternative Preparation of (E)-1,1,1,4,5,5,5-heptafluoro-4-(trifluoromethyl)pent-2-ene ($F_{13}$iE)

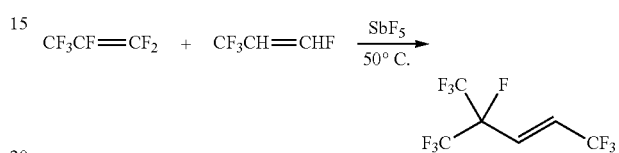

A 400 mL shaker tube was loaded 10 g of freshly distilled antimony pentafluoride ($SbF_5$). The tube was closed, cooled with dry ice, evacuated, and charged with 75 g of hexafluoropropene. The shaker tube was heated to 50° C. and HFO-1234ze was injected in 20 g increments (40 g total). Heating was continued for 12 h. 100 mL of water was injected into the reactor and the shaker tube was vented and unloaded. 90 g of crude reaction mixture was isolated, containing ~60% (E)-1,1,1,4,5,5,5-heptafluoro-4-(trifluoromethyl)pent-2-ene, along with dimers of HFO-1234ze (confirmed via GC/MS).

The reaction mixture was fractionated using 50 cm Vigroux distillation column to afford 54 g (50% yield) of (E)-1,1,1,4,5,5,5-heptafluoro-4-(trifluoromethyl)pent-2-ene. b.p. 48-49° C. (ratio E/Z isomers 97:3). The title product was identified by comparison with authentic sample, prepared by independent method. $^{19}$F NMR ($CDCl_3$): −65.91(3F, dd, 3.8, 1.8 HZ), −76.75 (6F, d, 7.6 Hz), −187.43 (1F, m) ppm; $^1$H NMR ($CDCl_3$): 6.44 (m) ppm; MS (m/z): 264 (M*, $C_6H_2F_{10}^+$).

OTHER EMBODIMENTS

1. In some embodiments, the present application provides a process of preparing (E)-1,1,1,4,5,5,5-heptafluoro-4-(trifluoromethyl)pent-2-ene, comprising reacting hexafluoroprop-1-ene with 1,3,3,3-tetrafluoroprop-1-ene in the presence of an acid catalyst.

2. The process of embodiment 1, wherein the acid catalyst is a Lewis acid catalyst.

3. The process of embodiment 1, wherein the acid catalyst is a strong Lewis acid catalyst.

4. The process of embodiment 1, wherein the acid catalyst is selected from $SbF_5$, aluminum chlorofluoride (ACF), and aluminum chloride.

5. The process of embodiment 1, wherein the acid catalyst is $SbF_5$.

6. The process of any one of embodiments 1 to 5, wherein the reacting is performed at a temperature of from about −30° C. to about 100° C.

7. The process of any one of embodiments 1 to 5, wherein the reacting is performed at a temperature of from about 25° C. to about 75° C.

8. The process of any one of embodiments 1 to 5, wherein the reacting is performed at a temperature of from about 40° C. to about 60° C.

9. The process of any one of embodiments 1 to 8, wherein the reacting is performed at a pressure of from about 1 atm to about 25 atm.

10. The process of any one of embodiments 1 to 9, wherein the reacting is performed as a liquid phase reaction.

11. The process of any one of embodiments 1 to 10, wherein the process is performed in the absence of an additional solvent component.

12. The process of any one of embodiments 1 to 11, wherein the process comprises pre-mixing the hexafluoroprop-1-ene and the acid catalyst to form a first mixture, prior to the reacting with 1,3,3,3-tetrafluoroprop-1-ene.

13. The process of embodiment 12, wherein the mixing of hexafluoroprop-1-ene and the acid catalyst is performed in the liquid phase.

14. The process of embodiment 12 or 13, wherein the first mixture is a liquid.

15. The process of any one of embodiments 12 to 14, wherein the pre-mixing is performed at a pressure of from about 1 atm to about 25 atm.

16. The process of any one of embodiments 12 to 15, further comprising addition of the 1,3,3,3-tetrafluoroprop-1-ene to the first mixture, thereby forming the (E)-1,1,1,4,5,5,5-heptafluoro-4-(trifluoromethyl)pent-2-ene.

17. In some embodiments, the present application provides a process of preparing (E)-1,1,1,4,5,5,5-heptafluoro-4-(trifluoromethyl)pent-2-ene, comprising fluorinating 2,4-dichloro-1,1,1,5,5,5-hexafluoro-2-(trifluoromethyl)pentane in the presence of a catalyst.

18. The process of embodiment 17, wherein the fluorinating comprises reacting the 2,4-dichloro-1,1,1,5,5,5-hexafluoro-2-(trifluoromethyl)pentane in the presence of a fluorinating agent.

19. The process of embodiment 18, wherein about 6 to about 25 molar equivalents of fluorinating agent is used based on 1 equivalent of the 2,4-dichloro-1,1,1,5,5,5-hexafluoro-2-(trifluoromethyl)pentane.

20. The process of embodiment 18 or 19, wherein the fluorinating agent is selected from hydrogen fluoride, antimony trifluoride, antimony tetrafluoride, antimony pentafluoride, antimony trichloride/hydrogen fluoride, antimony tetrachloride/hydrogen fluoride, or any mixture thereof.

21. The process of any one of embodiments 17 to 20, wherein the fluorinating is performed as a liquid phase fluorination.

22. The process of any one of embodiments 17 to 21, wherein the fluorinating is performed at a temperature of from about 50° C. to about 150° C.

23. The process of any one of embodiments 17 to 22, wherein the fluorinating is performed at a pressure of from about 0 psig to about 600 psig.

24. The process of any one of embodiments 17 to 23, wherein the fluorinating agent is hydrogen fluoride.

25. The process of any one of embodiments 17 to 24, wherein the catalyst is a chromium catalyst.

26. The process of any one of embodiments 17 to 24, wherein the catalyst is selected from chromium oxyfluoride, chromium oxyfluoride on activated carbon, chromium oxyfluoride on graphite, chromium oxyfluoride on fluoride graphite, chromium oxyfluoride on fluoride alumina, chrome oxide, high surface area chromium oxide, fluorinated alumina, and chromium/nickel on fluoride alumina.

27. The process of any one of embodiments 17 to 20 and 24 to 26, wherein the fluorinating is performed as a gas phase fluorination.

28. The process of embodiment 27, wherein the fluorinating is performed at a temperature of from about 200° C. to about 400° C.

29. The process of embodiment 27 or 28, wherein the fluorinating is performed at a pressure of from about 0 psig to about 200 psig.

30. The process of any one of embodiments 17 to 29, wherein the catalyst is activated prior to the fluorinating.

31. The process of embodiment 30, wherein the activating comprises heating the catalyst to a temperature of from about 350° C. to about 400° C. for a first period of time.

32. The process of embodiment 31, wherein the heating for a first period of time is performed in the presence of nitrogen gas.

33. The process of any one of embodiments 30 to 32, wherein the activating further comprises heating the catalyst to temperature of from about 350° C. to about 400° C. in the presence of hydrogen fluoride, for a second period of time.

34. The process of embodiment 33, wherein the heating for a second period of time is performed in the presence of nitrogen, air, or a mixture thereof.

35. The process of any one of embodiments 17 to 34, wherein the 2,4-dichloro-1,1,1,5,5,5-hexafluoro-2-(trifluoromethyl)pentane is prepared according to a process comprising reacting 2,2-dichloro-1,1,1,3,3,3-hexafluoropropane with 3,3,3-trifluoroprop-1-ene in the presence of an iron catalyst and a trialkyl phosphate.

36. The process of embodiment 35, wherein the iron catalyst is iron metal.

37. The process of embodiment 35 or 36, wherein the trialkyl phosphate is a tri($C_{1-6}$ alkyl)phosphate.

38. The process of embodiment 36, wherein the tri($C_{1-6}$ alkyl)phosphate is tributyl phosphate.

39. The process of any one of embodiments 35 to 38, wherein the reacting is performed at a temperature of from about 50° C. to about 250° C.

40. In some embodiments, the present application provides a composition, comprising:
(i) (E)-1,1,1,4,5,5,5-heptafluoro-4-(trifluoromethyl)pent-2-ene; and
(ii) one or more compounds selected from:
(Z)-1,1,1,4,5,5,5-heptafluoro-4-(trifluoromethyl)pent-2-ene; hexafluoroprop-1-ene; and
1,3,3,3-tetrafluoroprop-1-ene.

41. The composition of embodiment 40, wherein the composition comprises about 2 to about 3 mole percent (Z)-1,1,1,4,5,5,5-heptafluoro-4-(trifluoromethyl)pent-2-ene.

42. The composition of embodiment 40 or 41, wherein the composition further comprises $SbF_5$.

43. In some embodiments, the present application provides a composition, comprising:
(i) (E)-1,1,1,4,5,5,5-heptafluoro-4-(trifluoromethyl)pent-2-ene; and
(ii) one or more compounds selected from:
(Z)-1,1,1,4,5,5,5-heptafluoro-4-(trifluoromethyl)pent-2-ene; hexafluoroprop-1-ene; and
1,3,3,3-tetrafluoroprop-1-ene;
wherein the composition is prepared according to the process of any one of embodiments 1 to 16.

44. In some embodiments, the present application provides a composition, comprising:
(i) (E)-1,1,1,4,5,5,5-heptafluoro-4-(trifluoromethyl)pent-2-ene; and (ii) one or more compounds selected from:
1,1,1,4,5,5,5-heptafluoro-2-(trifluoromethyl)pent-2-ene;
(E)-4-chloro-1,1,1,5,5,5-hexafluoro-4-(trifluoromethyl)pent-2-ene; and 1,1,1,5,5,5-hexafluoro-2-(trifluoromethyl)penta-2,3-diene.

45. The composition of embodiment 44, wherein the composition further comprises 2,4-dichloro-1,1,1,5,5,5-hexafluoro-2-(trifluoromethyl)pentane.

46. The composition of embodiment 44 or 45, wherein the composition further comprises hydrogen fluoride, chromium oxyfluoride, or a combination thereof.

47. In some embodiments, the present application provides a composition, comprising:
(i) (E)-1,1,1,4,5,5,5-heptafluoro-4-(trifluoromethyl)pent-2-ene; and
(ii) one or more compounds selected from:
1,1,1,4,5,5,5-heptafluoro-2-(trifluoromethyl)pent-2-ene;
(E)-4-chloro-1,1,1,5,5,5-hexafluoro-4-(trifluoromethyl)pent-2-ene;
1,1,1,5,5,5-hexafluoro-2-(trifluoromethyl)penta-2,3-diene; and
2,4-dichloro-1,1,1,5,5,5-hexafluoro-2-(trifluoromethyl)pentane;
wherein the composition is prepared according to the process of any one of embodiments 17 to 39.

48. In some embodiments, the present application provides a composition, comprising (E)-1,1,1,4,5,5,5-heptafluoro-4-(trifluoromethyl)pent-2-ene and 2,4-dichloro-1,1,1,5,5,5-hexafluoro-2-(trifluoromethyl)pentane, wherein the composition is prepared according to the process of any one of embodiments 17 to 39.

49. In some embodiments, the present application provides a composition, comprising:
(i) 2,4-dichloro-1,1,1,5,5,5-hexafluoro-2-(trifluoromethyl)pentane; and
(ii) one or more compounds selected from 2,2-dichloro-1,1,1,3,3,3-hexafluoropropane and 3,3,3-trifluoroprop-1-ene.

50. The composition of embodiment 49, wherein the composition further comprises iron metal, iron chloride, tributyl phosphate, or any combination thereof.

51. In some embodiments, the present application provides a composition, comprising:
(i) 2,4-dichloro-1,1,1,5,5,5-hexafluoro-2-(trifluoromethyl)pentane; and
(ii) one or more compounds selected from 2,2-dichloro-1,1,1,3,3,3-hexafluoropropane and 3,3,3-trifluoroprop-1-ene; wherein the composition is prepared according to the process of any one of embodiments 35 to 39.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

What is claimed is:

1. A process of preparing (E)-1,1,1,4,5,5,5-heptafluoro-4-(trifluoromethyl)pent-2-ene, comprising reacting hexafluoroprop-1-ene with 1,3,3,3-tetrafluoroprop-1-ene in the presence of an acid catalyst, wherein the acid catalyst is a Lewis acid catalyst.

2. The process of claim 1, wherein the acid catalyst is selected from $SbF_5$, aluminum chlorofluoride (ACF), and aluminum chloride.

3. The process of claim 1, wherein the acid catalyst is $SbF_5$.

4. The process of claim 1, wherein the reacting is performed at a temperature of from about −30° C. to about 100° C.

5. The process of claim 1, wherein the reacting is performed at a pressure of from about 1 atm to about 25 atm.

* * * * *